United States Patent [19]

Hawman

[11] Patent Number: 5,528,042
[45] Date of Patent: Jun. 18, 1996

[54] RETROSPECTIVELY DETERMINING THE CENTER OF ROTATION OF A SCINTILLATION CAMERA DETECTOR FROM SPECT DATA ACQUIRED DURING A NUCLEAR MEDICINE STUDY

[75] Inventor: Eric G. Hawman, Schaumburg, Ill.

[73] Assignee: Siemens Medical Systems, Inc., Iselin, N.J.

[21] Appl. No.: 490,213

[22] Filed: Jun. 14, 1995

[51] Int. Cl.$^6$ ..................................................... G01T 1/166
[52] U.S. Cl. ...................................... 250/363.04; 250/369
[58] Field of Search ............................... 250/363.04, 369; 128/659, 653.1; 364/413.13, 413.15, 413.16, 413.19, 413.21, 413.22, 413.24

[56] References Cited

U.S. PATENT DOCUMENTS 4,582,995  4/1986  Lim et al. ........................... 250/363.04
4,692,624  9/1987  Ichihara .............................. 250/363.04

*Primary Examiner*—Davis L. Willis
*Assistant Examiner*—Kiet T. Nguyen
*Attorney, Agent, or Firm*—Mark H. Jay

[57] ABSTRACT

Two conjugate views of a patient are acquired during a SPECT nuclear medicine study. A common anatomical feature is identified in the views. Based on the differences in location of the common feature in the views, the center of rotation ("COR") of the detector during the study can be calculated after the study has been concluded. This COR can then be used during image reconstruction to determine the location at which each filtered view is backprojected. The resulting SPECT data is of higher quality because COR artifacts in the reconstructed image are reduced or eliminated.

5 Claims, 3 Drawing Sheets

RETROSPECTIVELY DETERMINING THE CENTER OF ROTATION OF A SCINTILLATION CAMERA DETECTOR FROM SPECT DATA ACQUIRED DURING A NUCLEAR MEDICINE STUDY

BACKGROUND OF THE INVENTION

The invention relates to nuclear medicine, and more particularly relates to nuclear medicine SPECT studies. In its most immediate sense, the invention relates to SPECT studies that are carried out using parallel hole collimators.

In nuclear medicine studies, a radioisotope is administered to a patient and taken up in an organ of interest (e.g. the heart). The radioisotope then undergoes radioactive decay, giving off gamma radiation in the process. In Single Photon Emission Computed Tomography (SPECT) studies, a collimated detector rotates at least 180° around the patient's body axis and detects the emitted gamma radiation. From this, it is possible to "reconstruct" a three-dimensional image that shows the locations within e.g. the heart where the radioisotope is taken up.

All SPECT reconstruction algorithms are based on an assumption that the coordinates of the scintillation camera system (as determined by the electronics within one or more camera detectors) correspond well to the physical coordinates of the patient. If such a correspondence is imprecise, the spatial resolution of the reconstructed SPECT images will be degraded; if such a correspondence is lacking, ring-shaped distortions (ring "artifacts") will appear in the reconstructed image.

Where the SPECT study is carried out using a focussing collimator (e.g. a collimator of the fan beam, cone beam or astigmatic type) other parameters must as well be made to correspond to the physical position of the patient. These parameters are, e.g., the radius of rotation of the detector, the x and y coordinates of the principal ray of the collimator and the focal length of the collimator.

One way to keep the coordinates of the scintillation camera system in close correspondence with the physical coordinates of the patient is to empirically determine the center of rotation ("COR") of the camera and to physically arrange the patient so that the necessary correspondence is achieved. Although this produces satisfactory results, it is inconvenient because the COR of the camera does not remain in a fixed location. COR errors arise from many sources (e.g. drift in the gains and offsets of the photodetectors in the scintillation camera detector(s), changes in camera collimation, flexure of the camera gantry) and change with time. It is therefore necessary to periodically (advantageously, monthly) redetermine the COR for each collimator that is used with the camera, using a special SPECT recalibration routine and a line of radioactive point sources.

SUMMARY OF THE INVENTION

It would be advantageous to provide a method whereby a SPECT study could be carried out and the COR of the study determined retrospectively. Such a retrospectively determined COR would more accurately reflect the current state of the scintillation camera system. This in turn would make it possible for the patient's body coordinate system to more precisely correspond to the coordinate system of the scintillation camera system, leading to a higher quality SPECT image with reduced artifact levels.

One object of the invention is to provide a method for retrospectively determining the center of rotation of a scintillation camera detector from image data acquired during a SPECT study.

Another object is, in general, to improve on known methods for image reconstruction in nuclear medicine.

In accordance with the invention, a scintillation camera is used to carry out a SPECT study in which the detector is caused to rotate at least 180° around the patient. A pair of conjugate views (i.e. two sets of image data, the sets being acquired at detector positions which are diametrically opposed views of the patient) of the patient is acquired. In each view, a common anatomical feature is identified and located. Then, the center of rotation of the study is calculated based upon the difference between the locations of the common feature in the views.

Advantageously, and in accordance with the preferred embodiment, the anatomical feature is the patient's body contour. Further advantageously, and also in accordance with the preferred embodiment, the step of identifying and localizing is carried out by acquiring a scatter image of the patient and using an edge detection algorithm on the scatter image.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
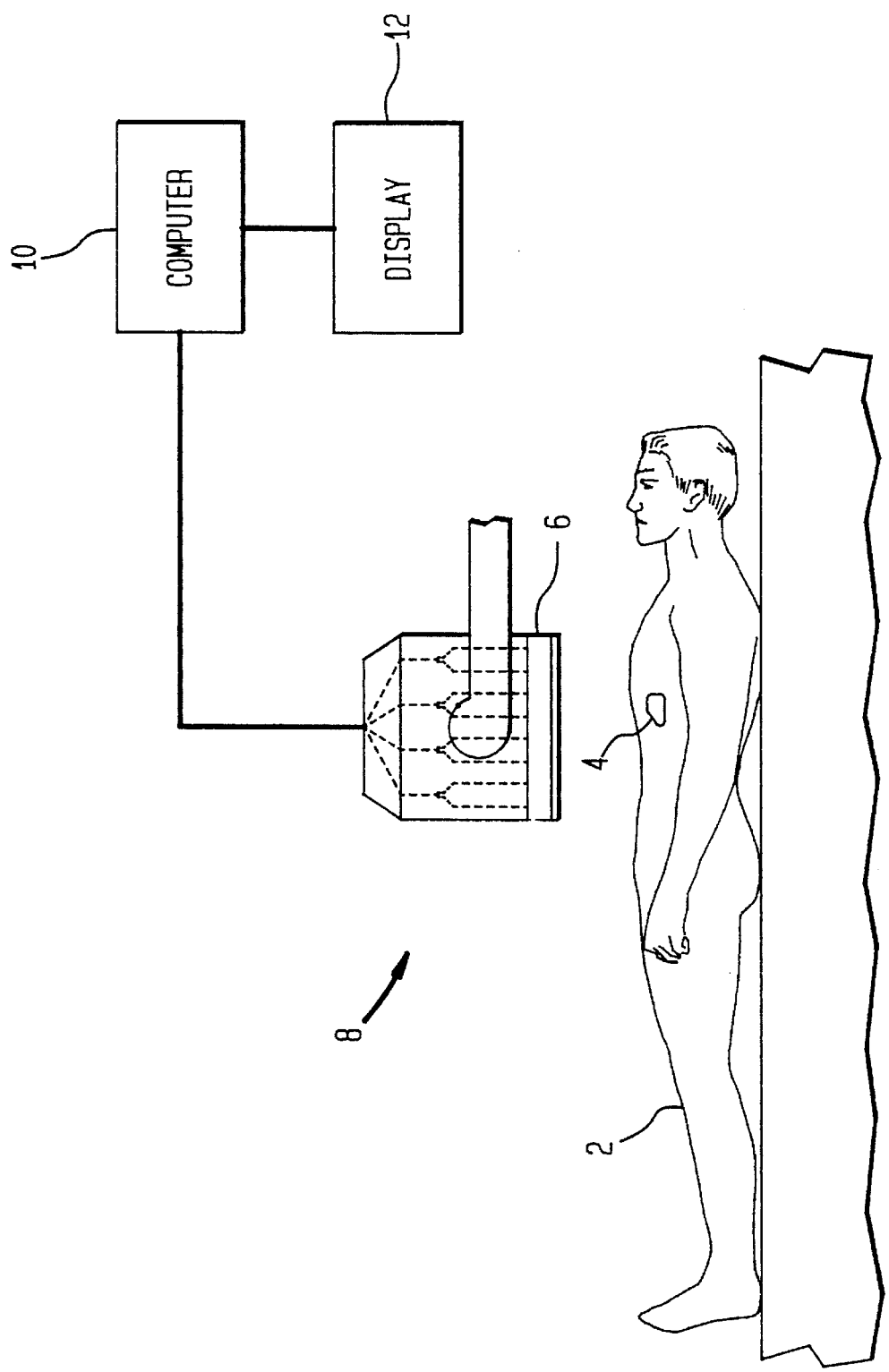
FIG. 1 schematically illustrates a SPECT study being carried out on patient.

FIG. 1 illustrates a SPECT study being conducted on a patient 2. A radioisotope (not shown) is administered to the patient 2, and the radioisotope is taken up in the heart 4. The radioisotope in the heart 4 decays by radioactive decay, and in the process gives off gamma radiation (not shown). This radiation is collimated by a collimator 6 (e.g. a parallel hole collimator) and detected by a detector 8. Information output from detector 8 is routed to a computer 10, which reconstructs an image (not shown) of the heart 4. This image may be displayed on a display 12.

In SPECT, the detector 8 is rotated around the patient 2; advantageously, the center of rotation (COR) is located in the heart 4. The detector 8 is rotated at least 180°, and advantageously 360°, around the patient 2. In the course of the study, the detector 8 is rotated to predetermined positions (stations) around the patient 2.

Conventionally, the task of calibrating the COR of the detector 8 requires time and attention from a technician. Even if the technician is careful, setup errors can occur, and such errors cause artifacts to appear in the reconstructed image (not shown). In accordance with the invention, the setup task is made easier, because the COR of the detector 8 is determined retrospectively, i.e. after the study has been concluded.

The invention proceeds from the realization that when a scintillation camera detector rotates through 180° in a SPECT study, the same anatomic feature as it appears in conjugate views must be equidistant from the COR of the detector.

Figure 2:
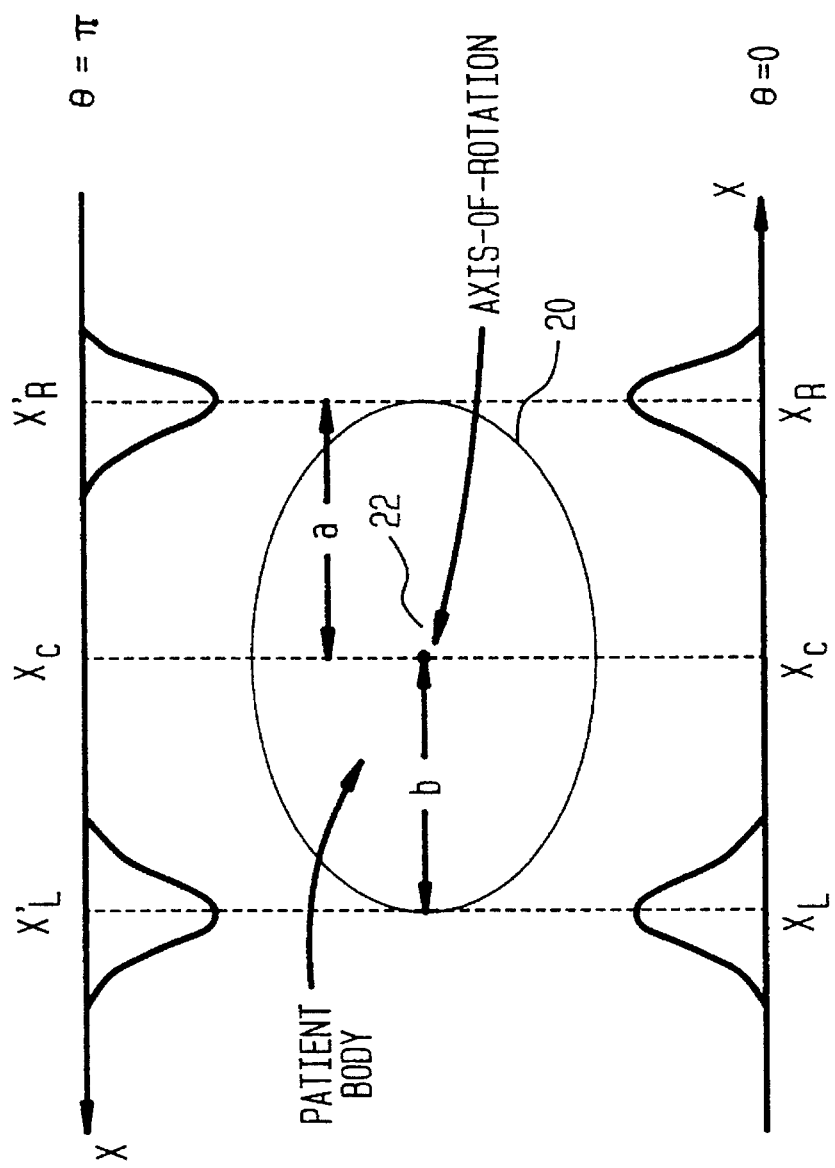
FIG. 2 is schematic illustration of the mathematical principles of an algorithm used in the preferred embodiment of the invention.

This is schematically illustrated in FIG. 2. In FIG. 2, the collimated detector 8 is shown in two diametrically opposed positions (the station wherein θ=0 radians and the station wherein θ=π radians). The result is two conjugate views of the body contour 20 of the patient 2.

The body contour 20 can be machine-identified by acquiring a scatter image of the patient 2 and applying an edge detection algorithm to the images acquired by the detector 8. When the detector 8 is at the station θ=0 radians, the X coordinate of the right edge of the body contour 20 is $X_R$ and the X coordinate of the left edge of the body contour 20 is $X_L$. When the detector 8 is at the station θ=π radians, the X coordinate of the right edge of the body contour 20 is $X'_R$ and the X coordinate of the left edge of the body contour 20 is $X'_R$. Since the detector 8 rotates around the COR 22 with a constant radius, it follows that for the right edge of the body $$\left. \begin{array}{c} X_R = X_C + a \\ X'_R = X_C - a \end{array} \right\} \rightarrow X_C = \frac{(X_R + X'_R)}{2}$$

and similarly, for the left edge of the body $$X_C = \frac{(X_L + X'_L)}{2}$$

The body contour 20 need not be the feature of interest. Another anatomical feature may be computer-identified and used instead. (U.S. Pat. No. 5,381,791 teaches methodology by which anatomical features may be computer-identified within nuclear medicine images). Furthermore, although it is advantageous to computer-identify the feature of interest, this is not required.

Figure 3:
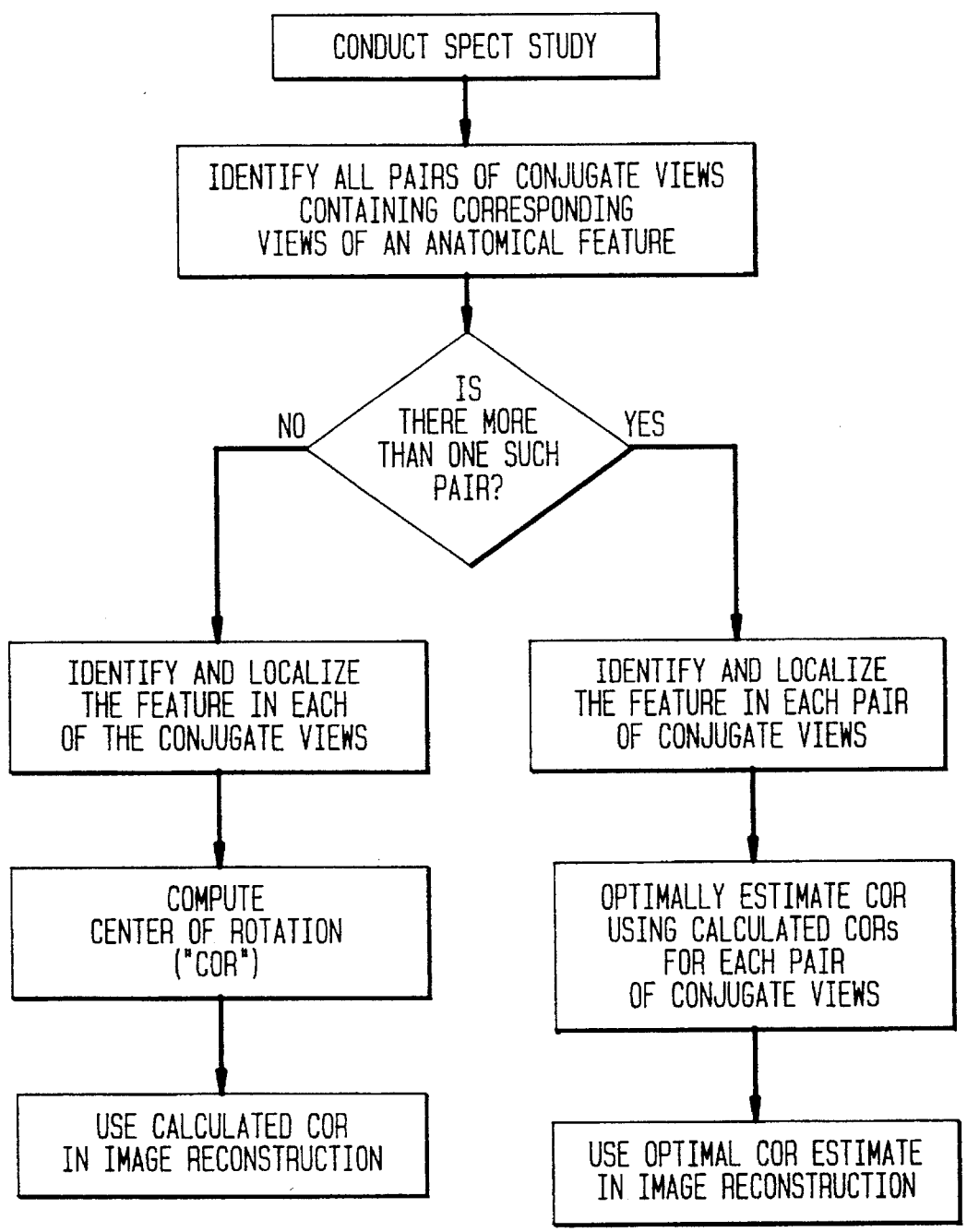
FIG. 3 is a flowchart illustrating a preferred embodiment of the invention.

FIG. 3 shows the preferred embodiment of the invention in flow-chart form. Initially, a nuclear medicine SPECT study is carried out on a patient using a parallel hole collimator; during the study, the detector may rotate as little as 180° or as much as 360°. Therefore, during the process of carrying out the study, at least one pair (and possibly many pairs) of conjugate views of the patient are acquired. If one pair of conjugate views is acquired, this feature is identified and localized. Thereafter, the COR of the study is calculated as described above.

If more than one conjugate view has been acquired, all conjugate views are processed to identify all conjugate pairs which contain corresponding anatomical features. If there is more than one conjugate pair having corresponding features, then the locations of the features provide a multiplicity of equations similar to those set forth above. This multiplicity of equations provides for the overdetermination of the COR. Optimally weighting and averaging the various COR estimates will produce an end result which is of higher accuracy than one produced only on the basis of a single conjugate pair.

If the anatomical feature is the patient's body contour, this identification and localization is carried out by acquiring a scatter image of the patient and using an edge detection algorithm.

The calculated COR is used in the reconstruction to determine the location at which each filtered view is backprojected. Since the COR has been determined on the basis of the most current information, the calculated COR is as current as possible and is little affected by system drift or by obsolete data. The result is an improvement of SPECT image quality.

Although a preferred embodiment has been described above, the scope of the invention is limited only by the following claims:

I claim:

1. A method of retrospectively determining the center of rotation of a scintillation camera detector from image data acquired during a SPECT study in which the detector is caused to rotate at least 180°, comprising the following steps:

acquiring a pair of conjugate views;

identifying and localizing, in each of the views, a common anatomical feature; and calculating, based upon a difference between the locations of said feature in the views, the center of rotation of the study.

2. The method of claim 1, wherein the common anatomical feature is a patient's body centour.

3. The method of claim 1, wherein the step of identifying and localizing comprises the steps of acquiring a scatter image of the patient and using an edge detection algorithm on said scatter image.

4. The method of claim 1, wherein the acquiring step is carried out using a focussing collimator.

5. The method of claim 4, further comprising the step of backprojecting the filtered image data.

\* \* \* \* \*